United States Patent [19]

Oxford et al.

[11] Patent Number: 4,997,841
[45] Date of Patent: Mar. 5, 1991

[54] INDOLE DERIVATIVES

[75] Inventors: Alexander W. Oxford, Royston; Darko Butina, Arlesey; Martin R. Owen, Puckeridge, all of United Kingdom

[73] Assignee: Glaxo Group Limited, England

[21] Appl. No.: 231,274

[22] Filed: Aug. 12, 1988

[30] Foreign Application Priority Data

Aug. 13, 1987 [GB] United Kingdom ............... 8719167
Jun. 14, 1988 [GB] United Kingdom ............... 8814002
Jun. 17, 1988 [GB] United Kingdom ............... 8814481

[51] Int. Cl.$^5$ .................. A61K 31/445; C07D 401/04
[52] U.S. Cl. ..................... 514/323; 514/339; 546/201; 546/273
[58] Field of Search ................ 546/201; 514/323

[56] References Cited

U.S. PATENT DOCUMENTS

| | | | |
|---|---|---|---|
| 4,278,677 | 7/1981 | Nedelec et al. | 546/273 |
| 4,530,932 | 7/1985 | Clemence et al. | 546/273 |
| 4,548,939 | 10/1985 | Kennis et al. | 514/265 |
| 4,711,893 | 12/1987 | Hausberg et al. | 514/339 |

FOREIGN PATENT DOCUMENTS

| | | |
|---|---|---|
| 0147107 | 7/1985 | European Pat. Off. |
| 0200322 | 11/1986 | European Pat. Off. |
| 1556919 | 11/1979 | United Kingdom . |
| 2124210A | 2/1984 | United Kingdom . |
| 2150932A | 7/1985 | United Kingdom . |
| 2162522A | 2/1986 | United Kingdom . |
| 2168973A | 7/1986 | United Kingdom . |

OTHER PUBLICATIONS

Guillaume et al., *Eur. J. Med. Chem.* 22, 1987, 33-43.
Peroutka et al., *J. Pharm. Exp. Ther.*, 237 (3), 901-906 (1986).
Taylor et al., *J. Pharm. Exp. Ther.*, 236 (1), 118-125 (1986).

*Primary Examiner*—Jane T. Fan
*Attorney, Agent, or Firm*—Bacon & Thomas

[57] ABSTRACT

Compounds are disclosed of formula (I)

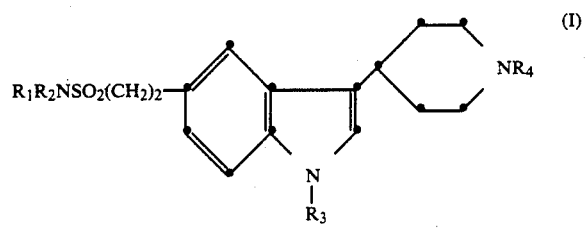

wherein
$R_1$ represents H or $C_{1-6}$ alkyl;
$R_2$ represents H or $C_{1-6}$ alkyl;
$R_3$ represents H;
$R_4$ represents H or $C_{1-3}$ alkyl; and pharmaceutically acceptable salts and solvates (for example hydrates thereof.

The compounds are indicated as useful for the treatment of migraine, cluster headache, chronic paroxysmal hemicrania and headache associated with vascular disorders.

Processes and intermediates for their preparation and pharmaceutical compositions containing them are also disclosed.

18 Claims, No Drawings

INDOLE DERIVATIVES

This invention relates to in dole derivatives, to processes for their preparation, to pharmaceutical compositions containing them and to their medical use, in particular to compounds and compositions of use in the treatment of migraine.

It has been suggested that the pain of migraine may be associated with excessive dilation of the cranial vasculature and known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an antiemetic but such treatments are of limited value.

More recently, indole derivatives which are selective $5HT_1$-like receptor agonists and which exhibit selective vasoconstrictor activity have been described in the art as useful in the treatment of migraine (see for example A. Doenicke, J. Brand, V. L. Perrin, *Lancet*, 1988, 1309–1311).

We have now found a novel group of indole derivatives which not only exhibit $5HT_1$-like receptor agonist activity and selective vasoconstriction but also unexpectedly have an enhanced overall bioavailability index following administration, in particular following non-parenteral administration.

Thus the invention provides in a first aspect an indole of formula (I).

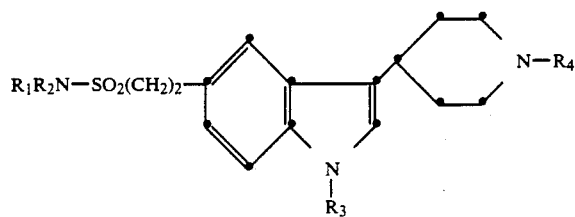

wherein
$R_1$ represents a hydrogen atom or a $C_{1-6}$ alkyl group;
$R_2$ represents a hydrogen atom or a $C_{1-6}$ alkyl group;
$R_3$ represents a hydrogen atom, $R_4$ represents a hydrogen atom or a $C_{1-3}$ alkyl group and pharmaceutically acceptable salts and solvates (for example hydrates) therof.

All optical isomers of compounds of general formula (I) and their mixtures including the racemic mixtures thereof are embraced by the invention.

As used herein, an alkyl group may be a straight chain (such as a methyl or ethyl) or branched chain alkyl group.

Suitable pharmaceutically acceptable salts of the indoles of general formula (I) include acid addition salts formed with organic or inorganic acids, for example, hydrochlorides, hydrobromimdes, sulphates, fumarates and maleates. Other salts may be useful in the preparation of compounds of formula (I), e.g. creatinine sulphate adducts.

A preferred class of compounds represented by the general formula (I) is that wherein $R_1$ represents a hydrogen atom or a $C_{1-3}$ alkyl group such as a methyl group.

Another preferred class of compounds is that wherein $R_2$ represents a hydrogen atom or a $C_{1-3}$ alkyl group such as methyl.

Conveniently, $R_1$ and $R_2$ together comprise from 1 to 3 carbon atoms.

The substituent $R_4$ is conveniently a $C_{1-3}$ alkyl group such as methyl.

Preferred compounds according to the invention include:
N-Methyl-3-(1-methyl-4-piperidinyl)-1H-indole-5-ethanesulphonamide;
N,N-Dimethyl-3-(1-methyl-4-piperidinyl)-1H-indole-5-ethanesulphonamide;
N-Ethyl-3-(4-piperidinyl)-1H-indole-5-ethanesulphonamide;
N-Methyl-3-(4-piperidinyl)-1H-indole-5-ethanesulphonamide;
3(1-Methyl-4-piperidinyl)-1H-indole-5-ethanesulphonamide;
and pharmaceutically acceptable salts and solvates thereof.

The selective $5HT_1$-like receptor agonist activity and selective vasoconstrictor activity of the compounds of the invention have been demonstrated in vitro. In addition, compounds of the invention selectively constrict the carotid arterial bed of the anaesthetised dog whilst having negligible effect on blood pressure.

Following non-parenteral, including intra-duodenal administration, the compounds of the invention show an enhanced bioavailability index in animals.

Compounds of the invention are useful in treating conditions associated with cephalic pain. In particular the compounds are useful in the treatment of migraine, cluster headache, chronic paroxysmal hemicrania and headache associated with vascular disorders and in alleviating the symptoms associated therewith.

Accordingly, the invention also provides a pharmaceutical composition which comprises at least one compound of formula (I) or a pharmaceutically acceptable salt or solvate (e.g. hydrate) thereof and formulated for administration by any convenient route. Such compositions are preferably in a form adapted for use in medicine, in particular human medicine, and can conveniently be formulated in conventional manner using one or more pharmaceutically acceptable carriers or excipients.

In a further aspect there is provided a compound of formula (I) or a salt or solvate thereof for use in therapy, in particular in human medicine. It will be appreciated that use in therapy embraces but is not necessarily limited to use of a compound of formula (I) or a salt or solvate thereof as an active therapeutic substance.

There is also provided as a further aspect of the invention the use of a compound of formula (I) in the preparation of a medicament for use in the treatment of conditions associated with cephalic pain in particular migraine, cluster headache, chronic paroxysmal hemicrania and headache associated with vascular disorders.

In an alternative or further aspect there is provided a method for the treatment of mammal, including man, comprising administration of an effective amount of a compound of formula (I) or salt or solvate thereof in particular in the treatment of conditions associated with cephalic pain and in alleviating the symptoms associated therewith.

It will be appreciated that reference to treatment is intended to include prophylaxis as well as the alleviation of established symptoms. Compounds according to the invention may be administered as the raw chemical but the active ingredient is preferably presented as a pharmaceutical formulation.

The active ingredient may conveniently be presented in unit dose form. A convenient unit dose formulation contains the active ingredient compound in an amount of from 0.1 mg to 100 mg.

The compounds according to the invention may for example be formulated for oral, sub-lingual buccal, parenteral, rectal or intranasal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

Tablets for sub-lingual administration may be formulated in a similar manner.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

It will be appreciated that the precise dose administered will depend on the age and condition of the patient, the particular compound used and the frequency and route of administration. The compound may be administered in single or divided doses and may be administered one or more times, for example 1 to 4 times per day.

A proposed dose of the compounds of the invention for oral, sublingual parenteral, buccal, rectal or intranasal administration to man (of approximately 70 kg bodyweight) for the treatment of migraine is 0.1 to 100 mg of the active ingredient per unit dose which could be administered, for example, 1 to 4 times per day.

For oral administration a unit dose will preferably contain from 2 to 50 mg of the active ingredient. A unit dose for parenteral administration will preferably contain 0.2 to 5 mg of the active ingredient.

Aerosol formulations are preferably arranged so that each metered dose or 'puff' delivered from a pressurized aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

Dosages of the compounds of the invention for rectal, sub-lingual or intranasal administration are similar to those for oral administration.

The compounds of the invention may, if desired, be administered in combination with one or more other therapeutic agents, such as analgesics, anti-inflammatory agents and anti-nauseants, and formulated for administration by any convenient route in conventional manner. Appropriate doses will be readily appreciated by those skilled in the art.

Compounds of formula (I) and pharmaceutically acceptable salts and solvates (e.g. hydrates) thereof, may be prepared by methods known in the art for the preparation of analogous compounds. In particular the compounds of formula (I) maybe prepared by the methods outlined below and which form a further aspect of the invention. In the following processes, $R_1$, $R_2$, $R_3$ and $R_4$, are as defined for formula (I) unless otherwise specified.

According to one general process (A) compounds of formula (I) may be prepared by reduction of the corresponding compounds of formula (II).

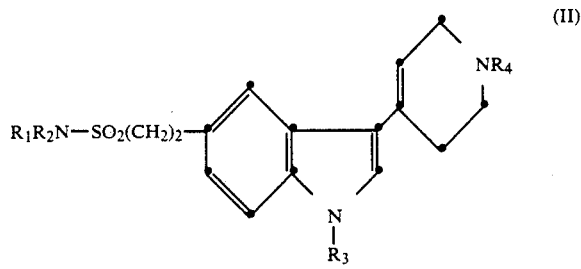

The compounds of formula (II) are themselves novel compounds and a further part of the invention. The compounds of formula (II) have also been found to be potent and selective vasoconstrictors.

The reduction process may conveniently be carried out in the presence of hydrogen and a noble metal catalyst, such as palladium, Raney nickel, platinum, platinum oxide or rhodium which may be supported, for example, on charcoal. Alternatively a homogenous catalyst such as tris(triphenylphosphine) rhodium chloride may be used. The reduction may be carried out in a solvent such as an alcohol e.g. methanol or ethanol, an ether e.g. dioxan, an ester e.g. ethyl acetate or an amide e.g. dimethylformamide and conveniently at a temperature of from $-10°$ to $+50°$ C.

The compounds of formula (II) may be prepared by condensing a compound of formula (III);

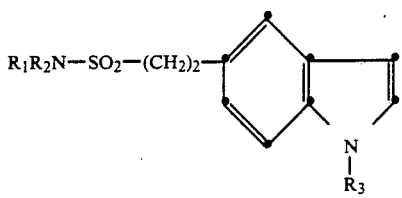

or a protected or activated derivative thereof, with a piperidone of formula (IV):

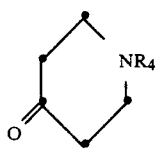

or a salt or protected derivative thereof.

The condensation reaction may be effected in a suitable reaction medium in the presence of an acid or a base, conveniently at a temperature of 25° to 120° C.

Acids which may be employed in the above process include organic and inorganic acids such as sulphonic acids (e.g. p-toluenesulphonic acid), carboxylic acids (e.g. acetic acid) and preferably strong inorganic acids such as polyphosphoric acid, sulphuric acid and hydrochloric acid. Suitable solvents for the reaction include inert solvents such as ethers (e.g. tetrahydrofuran or dioxan), alcohols (e.g. ethanol) and chlorinated hydrocarbons (e.g. chloroform or carbon tetrachloride). In some cases the acid may also act as the reaction solvent.

Bases which may be employed in the above process include alkali metal hydroxides (e.g. potassium hydroxide), alkali metal alkoxides (e.g. sodium or potassium methoxide, ethoxide or t- butoxide), alkali metal hydrides (e.g. sodium hydride) and alkali metal amides (e.g. sodamide). Suitable solvents for the reaction include alcohols (e.g. methanol or ethanol), ethers (e.g. tetrahydrofuran or dioxan) and dimethylsulphoxide.

Intermediates of formula (III) may be prepared by conventional methods for example by reacting an amine of formula $R_1R_2NH$ with the 3-unsubstituted analogs of compounds of formula (V) (as described hereinafter) using the methods described for process (B) hereinafter.

According to another general process (B), a compound of formula (I) may also be prepared by condensing an amine of formula $R_1R_2NH$ with an acid of formula (V)

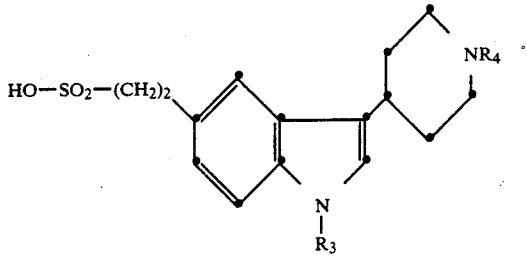

or an acylating agent corresponding thereto, or a salt (for example, an organic or inorganic acid addition salt such as the hydrochloride, hydrobromide, maleate, sulphate or creatinine sulphate adduct) or a protected derivative thereof.

Acylating agents corresponding to the acid of general formula (V) which may conveniently be used in the above process include acid halides, for example sulphonyl chlorides.

The condensation process involving the acylating agents may be effected in a suitable reaction medium and conveniently at a temperature of from $-70°$ to $+150°$ C. Thus the condensation reaction using an acid halide may be effected in a suitable reaction medium such as an amide (e.g. N,N'-dimethylformamide), an ether (e.g. tetrahydrofuran), a nitrile (e.g. acetonitrile), a haloalkane (e.g. dichloromethane) or mixtures thereof, optionally in the presence of a base such as pyridine or triethylamine or an inorganic base as calcium carbonate or sodium bicarbonate.

Where it is desired to prepare a compound of formula (I) in which $R_1$ and $R_2$ are both hydrogen atoms, ammonia may be used in the form of aqueous ammonia or in a solvent such as methanol.

Compounds of formula (V) and acylating agents corresponding thereto are novel and as such constitute a further feature of the invention. Compounds of formula (V) or acylating agents corresponding thereto may be prepared by methods analogous to those described in UK Patent Specification No. 2150932 and 'A Chemistry of Heterocyclic compounds—Indoles Part II', Chapter VI, edited by W. J. Houlihan (1972) Wiley Interscience, New York or by processes, such as process (A), as described herein.

According to another general process (C), a compound of formula (I) may be prepared by cyclisation of a compound of formula (VI)

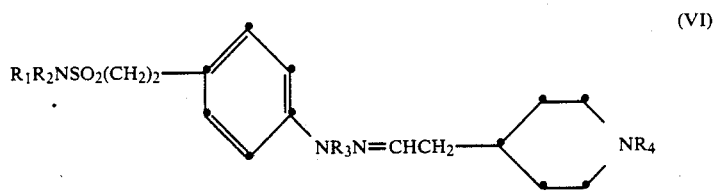

The process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Sons 1967).

Alternatively the cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be for example an inorganic acid such as concentrated hydrochloric, sulphuric or polyphosphoric acid. (In some cases the acid catalyst may also act as the reaction solvent). In an anhydrous reaction medium, which may comprise one or more alcohols or ethers (e.g. as described above) or esters (e.g. ethyl acetate), the acid catalyst will generally be a Lewis acid such as boron trifluoride, zinc chloride or magnesium chloride. The cyclisation reaction may conveniently be carried out at temperatures of from 20° to 200° C. preferably 50° to 125° C.

According to a particular embodiment of this process, compounds of formula (I) may be prepared directly by the reaction of a compound of formula (VII):

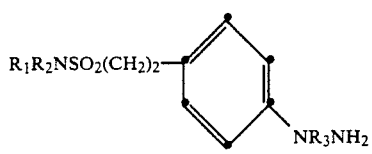

(VII)

or a salt thereof, with a compound of formula (VIII)

(VIII)

or a salt or protected derivative thereof (such as an acetal formed, for example, with an appropriate alkylorthoformate) using the appropriate conditions as described above. It will be appreciated that in this embodiment, a compound of formula (VI) is formed as an intermediate, and may be reacted in situ to form the desired compound of general formula (I).

Compounds of general formula (VI) may, if desired, be isolated as intermediates during the process for the preparation of compounds of formula (I) wherein a compound of formula (VII), or a salt or protected derivative thereof, is reacted with a compound of formula (VII), or a salt or protected derivative thereof, in water or in a suitable solvent, such as an aqueous alcohol (e.g. methanol) at a temperature of, for example, 20° to 100° C. If an acetal or ketal of a compound of formula (VIII) is used, it may be necessary to carry out the reaction in the presence of an acid (for example, acetic or hydrochloric acid).

Compounds of general formula (VII) may be prepared in a number of conventional steps, from compounds of formula (IX):

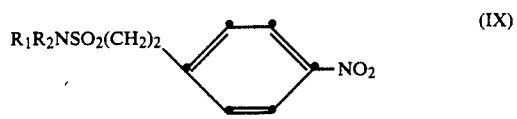

(IX)

For example, a compound of formula (IX) may be reduced by catalytic hydrogenation using a catalyst such as palladium on charcoal to give an amine which may be diazotised using, for example nitrous acid and the product of this reaction may then be reduced using, for example, stannous chloride to give a compound of formula (VII).

According to another general process (D), a compound of formula (I) may be prepared by reduction of a compound of formula (X)

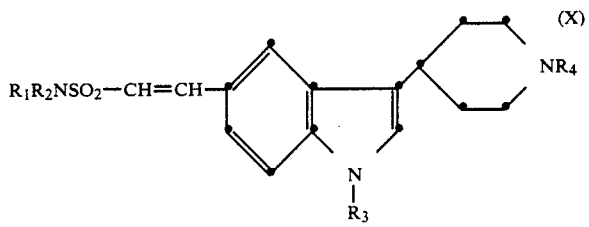

(X)

The reduction may be effected using similar reaction conditions to those described for general process (A) above.

Compounds of formula (X) are novel and form a further feature of the invention.

Compounds of formula (X) may be prepared by condensing a compound of formula (XI)

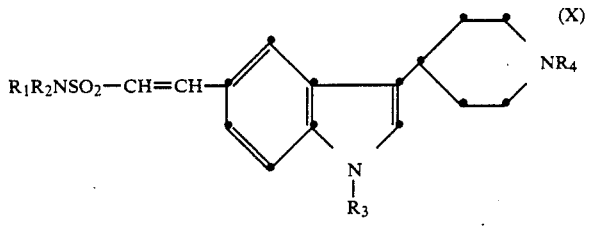

(X)

(wherein X represents a leaving atom or group such as a halogen atom for example a bromine atom) with an alkene $R_1R_2NSO_2CH=CH_2$.

The reaction will generally be effected in the presence of a palladium catalyst and a base. The catalyst may be, for example, palladium on charcoal or a palladium salt. Palladium salts which may be employed as catalysts include salts of organic acids such as acetates or salts of inorganic acids such as chlorides or bromides. The base may be, for example, a tertiary nitrogen base such as triethylamine or tri-n-butylamine or an alkali metal carbonate such as sodium carbonate. The reaction may optionally be carried out in the presence of a phosphine, for example a triarylphosphine such as triphenylphosphine or tri-o-tolylphosphine. A phosphine should be present when the process is effected with a compound of formula (XI) wherein X represents a bromine atom.

General process (D) may be effected in the presence or absence of solvent. An anhydrous or aqueous reaction medium comprising one or more solvents may be employed. Suitable solvents include nitriles, for example, acetonitrile, alcohols, for example methanol, amides, for example dimethylformamide, N-methylpyrrolidine or hexamethylphosphoramide; and water. The reaction may conveniently be carried out at a temperature of from 25° to 200° C., preferably 75° to 150° C.

Compounds of formula (XI) may be prepared from known compounds by methods analogous to those described herein.

According to another general process (E) a compound of formula (I) according to the invention may be converted into another compound of the invention using conventional procedures.

According to one embodiment of general process (E), a compound of general formula (I) wherein one or more of $R_1$, $R_2$ and $R_4$ represent hydrogen atoms may be alkylated using conventional techniques. The reaction may be effected using a suitable alkylating agent such as an alkyl halide, alkyl tosylate or dialkylsulphate. The alkylation reaction may conveniently be carried out in an inert organic solvent such as an amide (e.g. dimethylformamide) or an ether (e.g. tetrahydrofuran) preferably in the presence of a base. Suitable bases include, for example, alkali metal hydrides, such as sodium hydride, alkali metal carbonates, such as sodium carbonate or alkali metal alkoxides such as sodium or potassium methoxide, ethoxide or t-butoxide. The alkylation reaction is conveniently carried out at a temperature of from 25° to 100° C.

According to another general process (F), a compound of formula (I) where $R_2$ represents a $C_{3-6}$ alkyl group may be prepared by reduction of the corresponding compound (I) wherein $R_2$ represents a $C_{3-6}$ alkenyl group. The reduction process may be effected using the conditions as described above for the reduction of the group $CH=CH_2$ in compounds of formula (II). Compound analogous to compounds of formula (I) but in which $R_2$ represents a $C_{3-6}$ alkenyl group may be prepared by methods analogous to those described herein for the preparation of compounds of formula (I).

According to another general process (G), a compound of formula (I) according to the invention, or a salt thereof may be prepared by subjecting a protected derivative of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1981).

In compounds of formula (I) wherein $R_4$ represents hydrogen the group $NR_4$ may be protected for example by protonation or with a conventional amino protecting group. Such groups may include for example aralkyl groups, such as benzyl, diphenylmethyl or triphenyl groups; and acyl groups such as N-benzyloxycarbonyl or t-butoxycarbonyl. The indole nitrogen may also be protected, for example by an aralkyl group such as benzyl. Thus, compounds of general formula (I) wherein one or more of the groups $R_3$ and $R_4$ represent hydrogen may be prepared by deprotection of a corresponding protected compound.

Removal of any amino protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation.

As will be appreciated, in some of the general processes (A) to (F) described above it may be necessary or desired to protect any sensitive groups in the molecule as just described. Thus, a reaction step involving deprotection of a protected derivative of general formula (I) or a salt thereof may be carried out subsequent to any of the above described processes (A) to (F).

Thus, according to a further aspect of the invention, the following reactions may, if necessary and/or desired be carried out in any appropriate sequence subsequent to any of the processes (A) to (F).
(i) removal of any protecting groups; and
(ii) conversion of a compound of formula (I) or a salt thereof into a pharmaceutically acceptable salt or solvents (for example, hydrate) thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following Examples which should not be construed as constituting a limitation thereto. All temperatures are in °C.

INTERMEDIATE 1

N-Methyl-3-(1,2,3,6-tetrahydro-1-methyl-4-pyridinyl)-1H-indole-5-ethane sulphonamide oxalate A solution of N-methyl-1H-indole-5-ethanesulphonamide (1.0 g) in methanol (50 ml) containing potassium hydroxide (5.6 g) and N-methyl-4-piperidone (1.0 ml) was heated at reflux for 24h, cooled, and the resulting solid filtered off (1.0 g). A sample of the solid (0.2 g) was dissolved in a hot methanolic solution of oxalic acid (0.06 g), the solution cooled, and the salt precipitated by adding ethyl acetate (20 ml) and dry ether (50 ml). The salt was filtered off, and dried in vacuo to give the title compound as a solid (0.12 g) m.p. 87°-90° (shrinks) Analysis Found: C,52.2; H,5.6; N,9.5. $C_{17}H_{23}N_3O_2S.C_2H_2O_4.0.6H_2O$ requires C,52.5; H,6.0; N,9.7%.

INTERMEDIATE 2

5-Bromo-3-(1-methyl-4-piperidinyl)-1H-indole

A mixture of 5-bromoindole (39.2 g), N-methyl-4-piperidone (25.0 g) and potassium hydroxide pellets (12.0 g) in methanol 9250 ml) was stirred and heated at reflux for 17 h then cooled to 5°, with stirring. The mixture was filtered. The residue was washed consecutively with methanol, water, methanol again and ether and dried in vacuo to give the intermediate tetrahydropyridine (43.3 g) as a powder, with m.p. 256°–261° which was used without further characterisation in the next stage. A solution of ethanolic hydrogen chloride was prepared by adding acetyl chloride (20 ml) to ice-cooled, stirred ethanol (1.31). The intermediate tetrahydropyridine (43.2 g) was dissolved in a portion (0.951) of this solution. The hydrochloride salt of the intermediate precipitated out. In order to redissolve this salt the suspension was heated on a steam bath and portions of 2N hydrochloric acid (10 ml), water (15 ml) and con. (11N) hydrochloric acid (10 ml) were added. The resultant solution was added to a prehydrogenated suspension of 5% platinum oxide on carbon (7.0 g) in ethanolic (HCl (0.351 of the above solution) and the mixture was hydrogenated at room temperature and atmospheric pressure until uptake of hydrogen ceased. The mixture was filtered and the solvent was evaporated. The residue was suspended in ethyl acetate (600 ml). Sodium carbonate (2N; 350 ml) was added, with stirring and the mixture was filtered. The residue was washed with water and ethyl acetate and dried in vacuo to give the title compound (33.4 g) as a powder, m.p. 160°–165°.

INTERMEDIATE 3

5-Bromo-3-[1,2,3,6-tetrahydro-1-(phenylmethyl)-4-pyridinyl]-1H-indole

Freshly distilled 1-Benzyl-4-piperidone (11.7 g) was added to a stirred solution of 5-bromoindole (11.0 g) in 2M potassium hydroxide in methanol (81ml). The mixture was stirred at reflux for 8 h and then allowed to cool to 25° over 8 h. The solid was collected by filtration, washed with a mixture of methanol:water (2:1, 2×15 ml) and dried in vacuo at 50° for 18 h to give the title compound as a crystalline solid (18.6 g) m.p. 173°–175° (decomp).

INTERMEDIATE 4

5-Bromo-3-[1-(phenylmethyl)-4-piperidinyl]1H-indole

A solution of Intermediate 3 (4.00 g) in ethanolic hydrogen chloride (330 ml; prepared by the addition of acetyl chloride [1.65 g] to ethanol [250 ml] with stirring) was hydrogenated over 5% platinum on carbon (3.0 g) at room temperature and atmospheric pressure until hydrogenation was complete. The catalyst was removed by filtration. The solid was washed with ethanol (15 ml) and the combined filtrate evaporated to give an oily residue. The residue was partitioned between 2M aqueous sodium carbonate (75 ml) and ethyl acetate (175 ml), the phases separated and the aqueous layer re-extracted with ethyl acetate (100 ml). The combined organic layers were then washed with water (50 ml) extracted with saturated brine (50 ml), dried (MgSO$_4$) and the solvent evaporated to give the title compound as an oil (3.3 g). T.l.c. SiO$_2$CH$_2$CL$_2$:EtOH:0.88 NH$_3$ (100:8:1) Rf 0.44.

EXAMPLE 1

N-Methyl-3-(1-methyl-4-piperidinyl)-1H-indole-5-ethansulphonamide

Intermediate 1 (as the free base) (0.36 g, 0.001 mol) in absolute alcohol (70 ml) and anhydrous dimethylformamide (5 ml) was hydrogenated, in the presence of 5% palladium on activated carbon (0.36 g) at ambient temperature and atmospheric pressure. After 20 h, hydrogen absorption (25 cm$^3$, theoretical=24 cm$^3$) ceased. The catalyst was filtered off and the solvent removed in vacuo to given an opaque gun which solidified as a soft white solid (0.3 g). Purification by flash chromatography (Sorbsil C60 silica gel, CH$_2$CL$_2$EtOH/0.88 ammonia; 50:80:1) gave a colorless oil (0.21 g) that was triturated with ether to give the title compound (0.17 g) m.p. 156°–158°. T.l.c. SiO$_2$ (CH$_2$Cl$_2$/EtOH/0.88 ammonia; 50:8:1) Rf 0.4; detection, u.v., IPA.

Water assay Found: 0.12% w/w=0.02 mol equiv.

Analysis Found: C,60.5; H,7.3; N,12.1. C$_{17}$H$_{25}$N$_3$O$_2$S.O.O2H$_2$O requires C, 60.8; H, 7.5; N, 12.5%.

EXAMPLE 2

N-Methyl-3-(1-methyl-4-piperidinyl)-1H-indole-5-ethanesulphonamide (i)

(E)-N-Methyl-2-[3-(1-methyl-4-piperidinyl)-1H-indole-5-yl]ethenesulphonamide

A mixture of Intermediate 2 (1.00 g), N-methylethenesulphonamide (530 mg), tri-o-tolyphosphine (300 mg), palladium acetate (50 mg) and triethylamine (730 mg) in dry acetonitrile (added to give a total volume of 10 ml) was stirred and heated in a sealed vessel at 120° for 1.25 h and then at 80° for 16 h. The reaction was repeated on the same scale 10 times. In each case the sealed vessel was heated at 100°–110° for 3.5 h. The sealed vessels were cooled, the contents were combined and the solvent was evaporated. The reside was chromatographed on silica (450 g), using a mixture of dichloromethane, ethanol and ammonia (initially 80:8:1, gradually increasing the polarity to 65:8:1). The fractions containing the product were combined and evaporated to give a semi-solid. The material was briefly triturated in a mixture of cyclohexane and ethyl acetate (1:1; 100 ml) to give a solid which was filtered and dried to give the title compound (6.85 g) as a powder, m.p. 190°–192°.

(ii)

N-Methyl-3-(1-methyl-4-piperidinyl)-1H-indole-5-ethanesulphonamide

A solution of the product of stage (i) (5.78 g) in a mixture of ethanolic hydrogen chloride [prepared by adding acetyl chloride (1.71 g, 21.8 mmol) to IMS ethanol (400 ml) with stirring] and dimethylformamide (300 ml; added to the above to dissolve the starting material) was hydrogenated at room temperature and atmospheric pressure, using 10% palladium on carbon (5.00 g, 50% w/w with water) as the catalyst until uptake of hydrogen ceased. The mixture was filtered and the filtrate was evaporated to give a solid. The solid was partitioned between 2N sodium carbonate (60 ml) and ethyl acetate (200 ml) and the mixture was heated until the solid had dissolved. The phases were separated, the aqueous phase was extracted with ethyl acetate (200 ml) and the combined organic phases were washed with saturated brine (100 ml), dried (Na$_2$SO$_4$) and evaporated to give a gum. The gum was crystallised from ethyl acetate (60 ml) to give the title compound (4.30 g) as crystals, with m.p. 170°–171°

Analysis Found: C, 60.9; H, 7.6; N, 12.4. C$_{17}$H$_{25}$N$_3$O$_2$S requires C, 60.9; H, 7.5; N, 12.5%.

EXAMPLE 3

N-Methyl-3-(1-methyl-4-piperidinyl)-1H-indole-5-ethanesulphonamide

A solution of 4-hydrazino-N-methyl-benzenethanesulphonamide (0.5 g) and 1-methyl-4-piperidineacetaldehyde (0.35 g) in a mixture of water (10 ml) of 2N hydrochloric acid (1.0 ml, 2.00 mmol) was stirred for 2 days at room temperature. A further quantity of the aldehyde (0.35 g) was added and stirring continued for a further 30 min. The solution was then basified with 8% sodium bicarbonate to pH 8 and extracted with chloroform (3×50 ml). The combined organic extracts were dried ($Na_2SO_4$) and evaporated in vacuo to give the crude hydrazone as an oil (1.0 g). A solution of the hydrazone (1.0 g) in chloroform (20 ml) containing polyphosphate ester (10 g) was heated at reflux for 8 min. The solution was poured onto ice (200 g), stirred for 2 h treated with 2M sodium carbonate (20 ml) and extracted with chloroform (3×50 ml).

The combined organic extracts were dried ($Na_2SO_4$), evaporated in vacuo and the residue purified by flash chromatography (silica 9385, 100 g) eluting with $CH_2Cl_2/EtOH/NH_3$ (75:8:1) to give impure material as a yellow oil. Further flash chromatography (silica 9385, 100 g) eluting with $CH_2Cl_2/EtOH/NH_3$ (100:8:1) gave the product as an oil (0.05 g). This was crystallised from ethyl acetate to give the title compound.solid m.p. 156-157.

T.l.c. $SiO_2$, $CH_2Cl_2/EtOH/NH_3$ (50:8:1) Rf 0.6.

EXAMPLE 4

N,N-Dimethyl-3-(1-methyl-4-piperidinyl)-1H-indole-5-ethanesulphonamide

Sodium hydride (60% w/w with paraffin; 124 mg) was added cautiously to a stirred solution the product of Example 1 in dry dimethylformamide (20 ml). The resultant mixture was stirred at room temperature under nitrogen for 0.25 h then a solution of methyl iodide (440 mg) in dry dimethylformamide (1 ml) was added in a stream. The mixture was stirred at room temperature for 2.5 h. The reaction mixture was quenched with water (3 ml), evaporated in vacuo and the residue was chromatographed on silica (150 g), eluting with dichloromethane, ethanol and ammonia (80:10:1) to give a gum. The gum was briefly triturated in diethyl ether and the title compound crystallised out as a powder (238 mg), m.p. 170°-172°.

T.l.c. $SiO_2$ ($CH_2Cl_2:EtOH:NH_3$ 50:8:1). Rf 0.57.

EXAMPLE 5

(i)

(E)-N,N-Dimethyl-2[3-(1-methyl-4-piperidinyl)-1H-indol-5-yl]ethenesulphonamide

A mixture of 5-Bromo-3-(1-methyl-4-piperidinyl)-1-H-indole (2.0 g) N,N-dimethylenesulphonamide (1.184 g), tri-o-tolylphosphine (0.6 g) palladium acetate (0.1 ), triethylamine (1.0 ml) and anhydrous acetonitrile (12 ml) was heated in two 10 ml sealed vessels, with stirring at 107° (oil bath temp) for 2.25 h. The reaction mixtures were combined, the solvent removed by rotary evaporation and the residual foam purified by flash chromatography eluting with dichloromethane/ethanol/0.88 ammonia (100:8:1). Rotary evaporation of the appropriate fractions gave the product as a foam (1.92 g) T.l.c.

$SiO_2$ isoporopanol/ethanol/water/0.88 ammonia (20:20:8:1) Rf 0.5 (major)+0.55 (minor)+0.4 (trace).

(ii)

N,N-Dimethyl-3-(1-methyl-4-piperidinyl)-1H-indole-5-ethanesulphonamide

A solution of the product of stage (1) (1.5 g) in ethanol (200 ml) was added to a slurry of 5% palladium on activated carbon (1.5 g) in ethanol (100 ml). The resulting mixture was hydrogenated at 65 psi at room temperature for 17 h. The mixture was filtered and the filtrate evaporated to leave a solid (1.0 g) which was washed with isopropanol (3×20 ml) to give a solid (0.8 g) m.p. 215°-225°.

Crystallisation from hot ethanol (60 ml) gave the title compound as microneedles (0.29 g) m.p. 228°-232°.

T.l.c. $SiO_2$ isopropanol/ether/water/0.88 ammonium (20:20:8:1) Rf 0.5.

EXAMPLE 6

3-(1-Methyl-4-piperidinyl)-1H-indole-5-ethanesulphonamide (i)

(E)-2-[3-(1-methyl-4-piperidinyl)-1H-indol-5-yl]ethenesulphonamide

A mixture of Intermediate 2 (2.0 g), vinyl sulphonamide (0.88 g) palladium acetate (100 mg), tri(o-tolyl)-phosphine (0.6 g), triethylamine (1.0 ml), and acetonitrile (14 ml) was separated into two equal portions and placed into two sealed vessels (10 ml) and heated at 100° for 4 h. A further quantity of the vinyl sulphonamide (0.22 g) was added to each sealed vessel and the mixture was heated at 100° for a further 16 h. The resulting mixture was evaporated to dryness in vacuo and the residue purified by flash chromatography (silica 9385, 400 g) eluting with $CHCl_2/EtOH/NH_3$ (100:8:1 to 75:8:1) to give the title compound as a solid (0.8 g) m.p. 208°-209°.

(ii)

3-(1-methyl-4-piperidinyl)-1H-indole-5-ethanesulphonamide

A mixture of the product of stage (i) (0.8 g) in ethanolic hydrogen chloride (80 ml) was hydrogenated over pre-reduced 10% palladium on carbon (50% paste with water, 0.8 g) until uptake ceased. The catalyst was filtered off, washed with hot ethanol (50 ml) and the filtrate evaporated in vacuo to give crude material (0.15 g). The catalyst residues were then warmed (70°) with 2N hydrochloric acid (200 ml), filtered and the filtrate evaporated to dryness in vacuo (azeotroped with toluene). The residue was combined with the crude product obtained above and purified by flash chromatography (silica 9385, 100 g) eluting with $CH_2Cl_2/EtOH/NH_3$ (50:8:1) to give the title compound as a solid (0.2 g) m.p. >95° (foams), T.l.c. $SiO_2$, $CH_2Cl_2/EtOH/NH_3$ (25:8:1) Rf 0.5.

EXAMPLE 7

N-Methyl-3-(4-piperidinyl)-1H-indole-5-ethanesulphonamide hydrochloride (i)

(E)-N-Methyl-2-[3-[1-(phenylmethyl)-4-piperidinyl]-1H-indol-5-yl]ethenesulphonamide In each of three sealed vessels, a mixture of Intermediate 4 (1.10 g), N-methyl ethenesulphonamide (422 mg), triethylamine (843-882) tri-o-tolylphosphine (242 mg) and palladium acetate (39 mg) in dry acetonitrile (volume made up to 10 ml) was stirred and heated at 100° for 4 h. After cooling to 25° the contents of the vessels were combined and the solvent evaporated in vacuo at 40° to give an oily residue. This residue was purified by column chromatography on silica gel (Merck 7229, 300 g) eluting with a mixture of dichloromethane:ethanol:0.88 ammonia (300:8:1 to 200:8:1 to 100:8:1). The appropriate fractions were combined, and the solvent evaporated in vacuo to give the title compound as a foam (2.14 g).

T.l.c. $SiO_2$ $CH_2Cl_2$:EtOH:0.88 $NH_3$ (200:8:1) Rf 0.41.

(ii)
N-Methyl-3-(4-piperidinyl)-1H-indole-5-ethanesulphonamide hydrochloride

A solution of the product of stage (i) (2.14 g) in ethanolic hydrogen chloride [350 ml, prepared by the addition of acetyl chloride (860 mg) to ethanol (350 ml) with stirring] was hydrogenated over pre-reduced 10% palladium on charcoal (6.4 g) at 25° and 1 atmosphere pressure for 18 h. The reaction mixture was purged with nitrogen and a solution of ammonium formate (8.2 g) in methanol (100 ml) added. The mixture was stirred and brought to reflux under nitrogen for 10 min, cooled to 25° and the catalyst removed by filtration. Evaporation of the filtrate in vacuo gave a solid residue (8.5 g) which was redissolved in water (75 ml) and saturated with solid sodium chloride. The resultant precipitate was collected by filtration, washed with ice-cold water (1.5 ml) and ether (10 ml) and dried in vacuo at 45° for 18 h to give the title compound as a crystalline solid (640 mg) m.p. 253°-255°.

T.l.c. $SiO_2$ $CH_2Cl_2$:EtOH:0.88 $NH_3$ (25:8:1). Rf 0.14.

EXAMPLE 8

N-Ethyl-3-(4-piperidinyl)-1H-5-ethanesulphonamide (i)
(E)-N-Ethyl-2-[3-[1-(phenylmethyl)-4-piperidinyl]-1H-indol-5-yl]ethene sulphonamide Into each of two 10 sealed vessels were placed palladium acetate (50 mg), tri-o-tolylphosphone (300 mg), triethylamine (650 mg), N-ethylethenesulphonamide (275 mg) and Intermediate 4 (710 mg). Each mixture was made up to 10 ml with dry acetonitrile. The vessels were heated at 100° for 16 h then left at room temperature for 4 days. The contents of the sealed vessels were combined and the solvent and triethylamine were removed in vacuo. The residue was chromatographed on silica (205 mg; Merck 9385), eluting with dichloromethane, ethanol and ammonia (100:8:1) as the eluent, to give a foam (759 mg). The foam was crystallised from a hot mixture of ethyl acetate and cyclohexane to give the title compound (582 mg) as microcrystals m.p. 178°-180°.

(ii)
N-Ethyl-3-(4-piperidinyl)-1H-5-ethanesulphonamide

A solution of the product of stage (i) (370 mg) in ethanolic hydrogen chloride [prepared by adding acetyl chloride (105 mg, 1.34 mmol) to IMS ethanol (50 ml), with stirring] was hydrogenated over pre-reduced 10% palladium oxide on carbon (50% w/w with $H_2O$; 1.13 g), at room temperature and atmospheric pressure until uptake of hydrogen ceased. The mixture was filtered and the filtrate was evaporated to give a foam (280 mg) which was dissolved in methanol (4 ml). Sodium carbonate (2N; 2 ml) was added and the solvent was evaporated. THe residue was partitioned between water (10 ml) and ethyl acetate (50 ml). The aqueous phase was extracted with ethyl acetate (50 ml) and the combined organics were dried ($Na_2SO_4$) and evaporated to give a gum 235 mg) which was crystallised from a mixture of ethyl acetate and ether (10 ml; mainly ethyl acetate) to give the title compound (104 m g) as a powder m.p. 95°-100°.

T.l.c. $SiO_2$ $CH_2Cl_2$:EtOH:$NH_3$ (25:8:1). Rf 0.3.

EXAMPLE 9

N-Methyl-3-(1-methyl-4-piperidinyl)-1H-indole-5-ethanesulphonamide hydrochloride A solution of the product of Example 1 (50 mg) in hot ethanol (0.5 ml) was added to ethanolic hydrogen chloride [prepared by adding acetyl chloride (33 mg, 0.420 mmol) to ethanol (1 ml) at room temperature] in a stream with stirring at room temperature. A solid crystallised out from the initially clear solution. The suspension was stirred and cooled to 5° over 15 min then filtered under suction. The residue was washed with a little ethanol then dried at 60° in vacuo for 1 h to give the title compound (44 mg) as microcrystals, m.p. 237°-239°.

T.l.c. $SiO_2$ ($CH_2Cl_2$:EtOH:$NH_3$ 50:8:1). Rf 0.45.

The following examples illustrate pharmaceutical formulations according to the invention containing N-Methyl-3-(1-methyl-4-piperidinyl)-1H-indole-5-ethansulphonamide as the active ingredient. Other compounds of the invention may be formulated in a similar manner.

| TABLETS FOR ORAL ADMINISTRATION A. Direct Compression | |
|---|---|
| 1. | mg/tablet |
| Active ingredient | 49 |
| Magnesium Stearate BP | 0.65 |
| Anhydrous Lactose | 81 |

The active ingredient is sieved and blended with the anhydrous lactose and magnesium stearate. The resultant mix is compressed into tablets using a Manesty F3 tablet machine fitted with 8.0 mm concave punches.

| 2. | mg/tablet |
|---|---|
| Active ingredient | 49 |
| Magnesium Strearate BP | 0.7 |
| Microcrystalline Cellulose NF | 91 |

The active ingredient is sieved and blended with the microcrystalline cellulose and magnesium stearate. The resultant mix is compressed into tables using a Manesty F3 tablet machine fitted with 8.0 mm concave punches.

| B. WET GRANULATION | |
|---|---|
| | mg/tablet |
| Active ingredient | 7.0 |
| Lactose BP | 146.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using suitable diameter punches.

Tablets of other strengths may be prepared by altering the ratio of active ingredient to lactose or the compression weight and using punches to suit.

The tablets may be film coated with suitable film-forming materials, such as hydroxypropyl methylcellulose, using standard techniques. Alternatively the tables may be sugar coated, or enteric coated.

| CAPSULES | |
|---|---|
| | mg/capsule |
| Active ingredient | 49.00 |
| *Starch 1500 | 150.00 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | |
|---|---|
| Sucrose Free Presentation | mg/5 ml dose |
| Active Ingredient | 49.00 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

| SUSPENSION | |
|---|---|
| | mg/5 ml dose |
| Active ingredient | 49.00 |
| Aluminium monostearate | 75.00 |
| Sweetening agent | |
| Flavour | as required |
| Colour | |
| Fractionated coconut oil to | 5.00 ml |

The aluminium monostearate is dispersed in about 90% of the fractionated coconut oil. The resulting suspension is heated to 115° C. while stirring and then cooled. The sweetening agent, flavor and color are added and the active ingredient is suitably dispersed. The suspension is made up to volume with the remaining fractionated coconut oil and mixed.

| SUB-LINGUAL TABLET | |
|---|---|
| | mg/tablet |
| Active Ingredient | 49.00 |
| Compressible Sugar NF | 50.5 |
| Magnesium Stearate BP | 0.5 |
| Compression Weight | 100.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| SUPPOSITORY FOR RECTAL ADMINISTRATION | |
|---|---|
| Active ingredient | 49.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository molds.

| INJECTION FOR INTRAVENOUS ADMINISTRATION | |
|---|---|
| | mg/ml |
| Active Ingredient | 0.896 |
| Sodium Chloride Intravenous Infusion, BP, 0.9% w/v | to 1 ml |
| Batch Size | 2500 ml |

The active ingredient is dissolved in a portion of the Sodium Chloride Intravenous Infusion, the solution made to volume with the Sodium Chloride Intravenous Infusion, and the solution thoroughly mixed. The solution is filled into clear, Type I, glass 10 ml ampoules and sealed under a nitrogen headspace by fusion of the glass. The ampoules are sterilised by autoclaving at 121° C. for not less than 15 minutes.

| FOR INHALATION | |
|---|---|
| Inhalation Cartridges | mg/cartridge |
| Active ingredient (micronised) | 0.56 |
| Lactose BP | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

| Metered Dose Pressurised Aerosol | | |
|---|---|---|
| Suspension Aerosol | mg/metered dose | Per can |
| Active ingredient (micronised) | 0.280 | 73.92 mg |
| Oleic Acid BP | 0.020 | 5.28 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichloromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

| Nasal Spray | % w/v |
|---|---|
| Active Ingredient | 7.0 |
| Preservative | as required |
| Sodium Chloride BP | |
| Purified Water BP to | 100 |
| Shot Weight | 100 mg (equivalent to 7 mg active ingredient) |

The active ingredient, preservative and sodium chloride are dissolved in a portion of the water, the solution made to volume with the water and the solution thoroughly mixed.

The pH may be adjusted, using acid or alkali, to that of optimum stability and/or to facilitate solution of the active ingredient. Alternatively, suitable buffer salts may be used.

We claim:

1. A compound of formula (I)

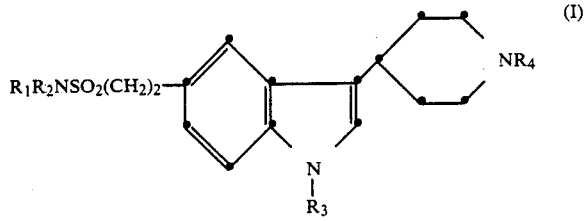

wherein
$R_1$ represents a hydrogen atom or a $C_{1-6}$ alkyl group;
$R_2$ represents a hydrogen atom or a $C_{1-6}$ alkyl group;
$R_3$ represents a hydrogen atom;
$R_4$ represents a hydrogen atom or a $C_{1-3}$ alkyl group;
or a pharmaceutically acceptable salt s solvate thereof.

2. A compound according to claim 1 wherein in the formula (I) $R_1$ represents a hydrogen atom or a $C_{1-3}$ alkyl group.

3. A compound according to claim 1 wherein in the formula (I) $R_2$ represents a hydrogen atom or a $C_{1-3}$ alkyl group.

4. A compound according to claim 1 wherein in the formula (I) $R_2$ represents a $C_{1-3}$ alkyl group.

5. A compound according to claim 1 wherein in the formula (I) $R_4$ represents a $C_{1-3}$ alkyl group.

6. A compound according to claim 1 which is N-Methyl-3-(1-methyl-4-piperidinyl)-1H-indole-5-ethanesulphonamide or a pharmaceutically acceptable salt or solvate thereof.

7. A compound according to claim 1 which is N,N-Dimethyl-3-(1-methyl-4-piperidinyl)-1H-indole-5-ethanesulphonamide or a pharmaceutically acceptable salt or solvate thereof.

8. A compound according to claim 1 which is N-Ethyl-3-(4-piperidinyl)-1H-indole-5-ethanesulphonamide or a pharmaceutically acceptable salt or solvate thereof.

9. A compound according to claim 1 which is N-Methyl-3-(4-piperidinyl)-1H-indole-5-ethanesulphonamide or a pharmaceutically acceptable salt or solvate thereof.

10. A compound according to claim 1 which is 3-(1-Methyl-4-piperidinyl)-1H-indole-5-ethanesulphonamide or a pharmaceutically acceptable salt or solvate thereof.

11. A pharmaceutical composition for use in the treatment of conditions associated with cephalic pain which comprises an effective amount to treat conditions associated with cephalic pain of at least one compound of formula (1) as defined in claim 1 or a pharmaceutically acceptable salt or solvate thereof together with one or more pharmaceutically acceptable carriers or excipients.

12. A pharmaceutical composition as claimed in claim 11 wherein the conditions associated with cephalic pain are migraine, cluster headache, chronic paroxysmal hemicrania or headache associated with vascular disorders.

13. A pharmaceutical composition according to claim 11 adapted for oral, parenteral or intranasal administration.

14. A pharmaceutical composition according to claim 11 which is formulated in unit dosage form comprising 0.1 mg to 100 mg of active ingredient.

15. A pharmaceutical composition according to claim 13 which is formulated in unit dosage form comprising 0.1 mg to 100 mg of active ingredient.

16. A method of treating a human susceptible to or suffering from migraine cluster headache, chronic paroxysmal hemicrania or headache associated with vascular disorders which comprises administering an effective amount of a compound of formula (I) as defined in claim 1 or a pharmaceutically acceptable salt or solvate thereof.

17. A method of treating a human susceptible to or suffering from migraine, cluster headache, chronic paroxysmal hemicrania or headache associated with vascular disorders which comprises administering a pharmaceutical composition according to claim 11.

18. A method of treating a human susceptible to or suffering from migraine, cluster headache, chronic paroxysmal hemicrania or headache associated with vascular disorders which comprises administering a pharmaceutical composition according to claim 13.

* * * * *

UNITED STATES PATENT AND TRADEMARK OFFICE

CERTIFICATE EXTENDING PATENT TERM
UNDER 35 U.S.C. § 156

PATENT NO.      :   4,997,841

ISSUED          :   March 5, 1991

INVENTORS       :   Alexander W. Oxford, et al.

PATENT OWNER    :   Glaxo Wellcome Inc.

PRODUCT         :   AMERGE® (naratriptan hydrochloride)

This is to certify that an application under 35 U.S.C. § 156 has been filed in the U.S. Patent and Trademark Office, requesting extension of the term of U.S. Patent No. 4,997,841 based upon the regulatory review of the product AMERGE® (naratriptan hydrochloride) by the Food and Drug Administration. Since it appears that the requirements of the law have been met, this certificate extends the term of the patent for the period of 694 days from August 12, 2008, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

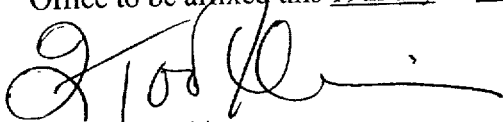

Q. Todd Dickinson
Under Secretary of Commerce for Intellectual Property and Director of the United States Patent and Trademark Office